(12) United States Patent
Suck et al.

(10) Patent No.: US 7,285,397 B1
(45) Date of Patent: Oct. 23, 2007

(54) INSECT POISON ALLERGENS WITH REDUCED IGE REACTIVITY AND METHOD PRODUCING THE SAME

(75) Inventors: Roland Suck, Hamburg (DE); Oliver Cromwell, Wentorf (DE); Helmut Fiebig, Schwarzenbek (DE)

(73) Assignee: Merck Patent GmbH, Darmstadt (DE)

( * ) Notice: Subject to any disclaimer, the term of this patent is extended or adjusted under 35 U.S.C. 154(b) by 504 days.

(21) Appl. No.: 10/148,565

(22) PCT Filed: Nov. 27, 2000

(86) PCT No.: PCT/EP00/11776

§ 371 (c)(1),
(2), (4) Date: Sep. 4, 2002

(87) PCT Pub. No.: WO01/40266

PCT Pub. Date: Jun. 7, 2001

(30) Foreign Application Priority Data

Dec. 1, 1999 (DE) ............................. 199 57 904

(51) Int. Cl.
- C07K 1/00 (2006.01)
- C07K 14/00 (2006.01)
- C07K 16/00 (2006.01)
- C07K 17/00 (2006.01)
- C12N 15/09 (2006.01)
- A23J 1/00 (2006.01)
- C12P 21/06 (2006.01)

(52) U.S. Cl. ............... 435/69.1; 435/69.1; 435/69.3; 435/71.1; 530/350; 530/412

(58) Field of Classification Search ............ 435/69.1, 435/69.3, 71.1; 530/350, 412
See application file for complete search history.

(56) References Cited

OTHER PUBLICATIONS

King et al., Hymenoptera Allergens, in Allergens and Allergen Immunotherapy, third edition, Marcel Dekker, Inc, 2004, pp. 339-353.*

Rudolph et al., FASEB J, 1996, 10:49-56.*
Cabrita et al., Biotechnol Annu Rev, 2004, 10:31-50.*
Fischer, BE. Biotech Adv 1994, 12:89-101.*
King, et al., "Murine T and B Cell Response to Natural and Recombinant Hornet Venom Allergen Do1 m 5.02 and its Recombinant Fragments", The Journal of Immunology, vol. 154, pp. 577-584, 1995.
Suck, et al., "Purification and Immunobiological Characterization of Folding Variants of the recombinant Major Wasp Allergen ves v 5 (Antigen 5)", International Archives of Allergy and Immunology, vol. 121, pp. 284-291, Apr. 2000.
Monsalve, et al., "Expressions of Recombinant Venom Allergen, Antigen 5 of Yellowjacket (Vespula Vulgaris) and Paper Wasp (Polistes Annularis), in Bacteria and Yeast", Protein Expression and Purification, vol. 16, pp. 410-416, Aug. 1999.
Forster et al., "Natural and Recombinant Enzymatically Active or Inactive bee venom Phospholipase A2 has the same Potency to Release Histamine from Basophils in Patients with Hymenoptera Allergy", The Journal of Allergy and Clinical Immunology, vol. 95, pp. 1229-1235, 1995.
Soldatova, et al., "Superior Biologic Activity of the Recombinant bee venom Allergen Hyaluronidase Expressed in Baculovirus-Infected Insect Cells as Compared with *Escherichia coli* ", The Journal of Allergy and Clinical Immunology, vol. 101, pp. 691-698, 1998.
Fang et al., "cDNA cloning and primary structure of a white-face hornet venom allergen, antigen 5", Proc. Natl. Acad. Sci. USA, vol. 85, pp. 895-899, Feb. 1988.

\* cited by examiner

*Primary Examiner*—Michail A. Belyavskyi
*Assistant Examiner*—Nora M. Rooney
(74) *Attorney, Agent, or Firm*—Millen, White, Zelano & Branigan, P.C.

(57) ABSTRACT

The invention relates to recombinant insect poison allergens and to a specific method for producing them. Said allergens can be varied according to whether they are produced using folds (conformations) that are identical or different to those that occur naturally. The proteins with folds that do not occur naturally have a reduced IgE reactivity or allergenity and can therefore be used as therapeutic agents in the immunotherapy of allergies.

14 Claims, 1 Drawing Sheet

Figure 1: Flow chart for the method rAg5 = recombinant antigen 5

```
┌─────────────────────────────┐
│     rAg5 inclusion bodies   │
└─────────────────────────────┘
              │
              ▼
┌─────────────────────────────┐
│       Denaturing with       │◄─────┐
│     guanidinium chloride    │      │
└─────────────────────────────┘      │
              │                      │
              ▼                      │
┌─────────────────────────────┐      │
│           Dialysis          │      │
│                             │      │
│  Cysteine    Sodium acetate buffer │
│         ↘      ↙            │      │
│        Distilled water      │      │
└─────────────────────────────┘      │
          │   │   │                  │ Pellet
          ▼   ▼   ▼                  │
┌─────────────────────────────┐      │
│       Centrifugation        │      │
└─────────────────────────────┘      │
                                     │
   ▲  ▶           ◀  ▲               │
┌─────────────────────────────┐      │
│   P    S         P    S     │──────┘
│   rAg5           rAg5       │
│   IgE-reactive   non-IgE-reactive │
│                             │
│      P = pellet  S = supernatant  │
└─────────────────────────────┘
```

INSECT POISON ALLERGENS WITH REDUCED IGE REACTIVITY AND METHOD PRODUCING THE SAME

The invention relates to recombinant insect poison allergens and to a method for targeted production thereof, where the said allergens can be differentiated by nature-identical or nature-contrary folds (conformations), depending on the performance of the production method.

An application of fold shapes which correspond to the natural molecule consists in single-allergen-differentiated diagnostics (in vitro or in vivo) of allergy sufferers, specifically insect poison allergy sufferers.

The nature-contrary fold shapes can be employed as therapeutic agents for specific immunotherapy which have low side effects. These recombinant fold variants could thus effect safer treatment than the natural product. The method is designed in such a way that biotechnological production can be carried out under conditions which are necessary for pharmaceuticals (GMP).

Insect sting allergies are caused principally by wasps and honey bees and can result in severe systemic symptoms or even potentially fatal anaphylaxia (Müller, U. R., in: Insect sting allergy, Gustav Fischer Verlag; 1990). The substances which trigger type 1 allergy are proteins, glycoproteins or polypeptides of the insect venom. These allergens react, after injection, with the IgE molecules bound to the surface of mast cells in sensitised persons. If FcεRI-bound IgE molecules of this type are crosslinked to one another by an allergen, this results in the release of mediators (for example histamine, leukotrienes) and cytokines by the effector cell and thus in the corresponding clinical symptoms.

Besides the peptide melittin, the enzymes hyaluronidase and phospholipase A2 act as allergenic constituents of bee venom (Habermann, E., 1972, Science 177, 314-322). In the case of the wasp, the main enzymatically active allergens are likewise a hyaluronidase, which is similar to that of bee venom (Hoffmann, D. R., 1986, J. Allergy Clin. Immunol. 78, 337-pairing the T-cell epitopes which are essential for the therapy (Schramm et al., 1999, J. Immunol. 162, 2406-2414).

It is known from heterologous expression in *E. coli* that most eukaryotic proteins do not adopt the 'natural' conformation or only do so to a small extent. A consequence of these incorrect folds is frequently insolubility of these proteins. This is observed in particular in cysteine-containing proteins (Kuchler et al., 1989, Eur. J. Biochem. 184, 249-254). It has been reported of antigen 5 in particular that expression in bacteria results in insoluble aggregates which do not have the natural conformation (Monsalve et al., 1999, Protein Express Purif. 16(3): 410-416). Insoluble aggregates of this type cannot be used either for diagnostics or for therapy.

The proteins which are insoluble in *E. coli* are frequently prepared for research purposes in a eukaryontic expression system, such as, for example, yeast or insect cells (Monsalve et al., 1999, Protein Express Purif 16(3): 410-416; Soldatova et al., 1998, J Allergy Clin Immunol 101: 691-698). However, disadvantages of eukaryontic expression systems are in particular possible hyperglycosylations (Grobe et al., 1999, Eur J Biochem 263: 33-40), proteolytic degradation processes and comparatively small product yields (Glover and Hames (eds.), 1995, Expression Systems, IRL Press, Oxford-New York-Tokyo). Proteins of this type are therefore usually unsuitable for allergological use in the sense of pharmaceutical-medical diagnostics and therapy.

The products of the method according to the invention which have the natural conformation can advantageously be used in in-vitro and in-vivo diagnostics of allergic disorders, especially insect sting allergy. This nature-identical fold shape is available for the detection of IgE antibodies in established methods.

On the other hand, the variants produced with the aid of the invention which are distinguished by an essentially non- or only partially IgE-reactive conformations can be used as hypoallergenic components in preparations for specific immunotherapy. The term "hypoallergenic" above and below is taken to mean, in accordance with the invention, reduced to absent, preferably from 5 to 95%, in particular from 20 to 85%, reduced allergeneity (compared with the natural allergen) due to a reduced IgE response.

The present invention is a method with which recombinant allergens can be produced in bacteria (*E. coli*). A first purification step takes place through considerable enrichment of the insoluble protein aggregates, These aggregates are then denatured without addition of reducing agents. Depending on the subsequent dialysis conditions, different fold shapes are obtained. It is crucial that these molecules are monomeric and soluble. The first soluble fold variant has an IgE reactivity which is comparable with that of the natural allergen and can accordingly be used for diagnostic purposes. A product of this type is obtained by dialysis with cysteine-containing solution.

The other alternative soluble fold variants are structurally different from the natural allergen and are distinguished by reduced or absent IgE reactivity. For this reason, variants of this type are suitable for facilitating improved immunotherapy. A hypoallergenic product of this type is obtained in accordance with the invention by dialysis with acidic buffers, preferably in a pH range between 3.5 and 6.5, in particular between 4.0 and 5.5.

The invention thus relates to recombinant insect allergen which is characterised in that it has reduced IgE reactivity or allergeneity. In accordance with the invention, the allergeneity of these proteins is reduced by up to 95% compared with the natural allergen.

In particular, the invention relates to a corresponding recombinant wasp insect allergen, in particular from *Vespula vulgaris, Paravespula* spec. and *Vespula germanica*.

The invention furthermore relates to a method for isolating essentially pure recombinant insect poison allergens which is characterised in that the allergenic proteins are produced in insoluble form as "inclusion bodies" in bacteria cells, the said insoluble aggregates are denatured, and the denatured products are converted by dialysis into soluble, monomeric allergens of different fold conformations and isolated. The said denaturing is preferably carried out using guanidinium chloride without addition of reducing agents.

The invention relates, in particular, to a method for isolating recombinant insect poison allergens with reduced allergeneity, or IgE reactivity, in which the dialysis is carried out using acidic buffer, preferably sodium acetate buffers having a pH of between 4.5 and 5.0.

However, the invention also relates to a method for isolating recombinant insect poison allergens with normal allergeneity, or IgE reactivity, in which the dialysis is carried out using cysteine-containing solutions.

The invention also relates to a recombinant wasp poison allergen which is obtainable by the corresponding method described above and below.

The invention furthermore relates to a pharmaceutical preparation which comprises a corresponding recombinant allergen with reduced or diminished IgE reactivity and corresponding adjuvants and excipients.

Finally, the invention relates to the use of insect poison allergens obtainable by a corresponding method described above or below for the in-vivo and in-vitro diagnosis of insect sting allergies.

The method is described in detail below:

By way of example, the wasp poison allergens antigen 5 from *Vespula vulgaris* (Ves v 5) and antigen 5 from *Vespula germanica* (Ves g 5) were cloned into the expression vector pSE420 and transformed into the K12 bacteria strain M15 pREP4. A flow chart for this method is shown in FIG. 1.

The recombinant allergens are produced using a preculture of the strain for inoculation of an expression culture. The expression, induced by IPTG, is carried out in a chicane flask at 37° C. in LB medium with limited oxygen supply (90 rpm/min). The bacteria are harvested by centrifugation (5000×g, 10 min, 20° C.) after expression for 5 hours. The bacterial digestion is carried out after resuspension of the cells in buffer (50 mM tris/HCl, 25% (w/v) sucrose, pH 8.0) by lysozyme addition (10 µg/g wet weight). This is followed by addition of the same volume of detergent solution (0.2 M NaCl, 1% (w/v) DOC, 1% (w/v) Nonidet P40). This digestion solution is subsequently treated with ultrasound (3 min on ice, 130 watts, 0.5 s pulse). Since the expression products are primarily in the form of insoluble aggregates (inclusion bodies), they can be separated from the majority of the remaining components (cell wall fragments, ribosomes, etc.) by centrifugation at 3000×g owing to their high density. The further purification is carried out by three successive washing steps with detergent-containing solutions (1% Triton X-100). The purified inclusion bodies are subsequently digested by addition of denaturing buffer (6M guanidinium chloride, 20 mM tris/HCl, pH 8.0) and shaken for 2 hours at RT.

In order to isolate IgE-reactive fold shapes, the denaturing batch is introduced into a dialysis tube (digestion limit 12-14 kDa) and dialysed against 100 times the volume of cysteine solution (5 mM cysteine) for 12 hours at RT with stirring. This is followed by dialysis against distilled water in order to remove the cysteine.

In order to obtain conformations with reduced IgE reactivity, the first dialysis will be carried out against 20 mM sodium acetate buffer (pH 5.0). Here too, further dialysis against distilled water is carried out. After removal, the water-soluble allergens are separated off from the precipitated aggregates by centrifugation. The supernatant contains the desired soluble recombinant allergens. Instead of sodium acetate buffer, it is also possible to use other acidic buffers which are capable of buffering in a range from 3.5 to 6.5, preferably from 4.0 to 5.5. Examples of buffer systems of this type are adequately described in the literature.

The precipitated recombinant allergens produced in both methods can be re-denatured and treated in accordance with the same scheme. This significantly increases the yield.

After the dialysis steps, the products have a purity of about 95%. Further purification steps of the basic insect poison allergens are cation exchange chromatography (buffer pH 7.2) with, for example, Source S (Pharmacia, Freiburg, Germany) and gel filtration. In addition to the removal of high- and low-molecular-weight minimal impurities, gel filtration also serves for desalination.

Quality control of the products is based on the following characteristic properties, which are summarised in tabular form for antigen 5: n–antigen=natural antigen

| Property | Fold with natural IgE reactivity | Fold with reduced IgE reactivity |
|---|---|---|
| Apparatus. MW in the SDS-page (non-reducing cond.) | 25 kDa | 26-27 kDa |
| Salt conc. for elution in Source S | 320 mM NaCl | 400 mM NaCl |
| Cleavage with protease V8 | 15 kDa fragment + peptides | peptides <10 kDa |
| Antigen 5 specific monoclonal antibodies | detection by 8E3, 1E11 | detection only possible with 8E3 |
| Frequency IgE reactivity with sera from allergy sufferers | >95% | <10% |
| Allergenic power | similar to n-antigen 5 | >10 x less than nAg5 |

The method according to the invention is suitable for all types of insect poison allergens. The purification techniques used and recombinant cloning and expression techniques are known and available to the person skilled in the art and can be replaced by known similar methods.

We claim:

1. A method of producing a soluble wasp poison allergen antigen 5 having reduced IgE reactivity, comprising
   expressing said wasp poison allergen antigen 5 in bacteria in an insoluble form as inclusion bodies,
   denaturing said inclusion bodies using guanidine chloride without addition of any reducing agent, and
   dialyzing said denatured product against an acidic buffer, wherein said acidic buffer does not comprise any reducing agent.

2. A method according to claim 1, wherein the sodium acetate buffer having a pH of between 4.5 and 5.0 is employed as the acidic buffer.

3. A method according to claim 1, wherein wasp poison allergen antigen 5 *Vespula* species are produced.

4. A method of claim 1, wherein said dialysis is performed with a buffer having a pH between 3.5 and 6.5.

5. A method of claim 1, wherein the wasp poison allergen antigen 5 is from *Vespula vulgaris* or *Vespula germanica*.

6. A method of claim 1, wherein the wasp poison allergen antigen 5 is from the *Paravespula* species.

7. A method of claim 1, wherein the bacteria is *E. coli*.

8. A method of claim 1, wherein the IgE reactivity is reduced by up to 95% compared with the natural allergen.

9. A method of claim 1, further comprising performing ion exchange chromatography on the soluble allergen antigen 5.

10. A method of claim 1, further comprising dialyzing the soluble allergen antigen 5 against distilled water.

11. A method of producing a soluble wasp poison allergen antigen 5 having normal IgE reactivity, comprising
    expressing said wasp poison allergen antigen 5 in bacteria in an insoluble form as inclusion bodies,
    denaturing said inclusion bodies using guanidine chloride without addition of any reducing agent, and
    dialyzing said denatured product against a solution containing cysteine.

12. A method of claim 11, further comprising dialyzing the soluble wasp poison allergen antigen 5 against distilled water.

13. A method of producing a soluble *Vespula* wasp poison allergen antigen 5 having reduced IgE reactivity, comprising
    expressing said *Vespula* wasp poison allergen antigen 5 in bacteria in an insoluble form as inclusion bodies,
    denaturing said inclusion bodies using guanidine chloride without addition of any reducing agent, and dialyzing said denatured product against an acidic buffer, wherein said acidic buffer does not comprise any reducing agent.

14. A method of producing a soluble *Vespula* wasp poison allergen antigen 5 having normal IgE reactivity, comprising expressing said *Vespula* wasp poison allergen antigen 5 in bacteria in an insoluble form as inclusion bodies, denaturing said inclusion bodies using guanidine chloride without addition of any reducing agent, and dialyzing said denatured product against a solution containing cysteine.

* * * * *

UNITED STATES PATENT AND TRADEMARK OFFICE
CERTIFICATE OF CORRECTION

PATENT NO. : 7,285,397 B1  Page 1 of 1
APPLICATION NO. : 10/148565
DATED : October 23, 2007
INVENTOR(S) : Suck et al.

It is certified that error appears in the above-identified patent and that said Letters Patent is hereby corrected as shown below:

Column 4, line 32, reads "A method" should read -- The method --
Column 4, line 32, reads "the sodium" should read -- a sodium --
Column 4, line 35, reads "A method" should read -- The method --
Column 4, line 36, reads "antigen 5 *Vespula*" should read -- antigen 5 from *Vespula* --
Column 4, line 37, reads "A method" should read -- The method --
Column 4, line 39, reads "A method" should read -- The method --
Column 4, line 41, reads "A method" should read -- The method --
Column 4, line 43, reads "A method" should read -- The method --
Column 4, line 44, reads "A method" should read -- The method --
Column 4, line 46, reads "A method" should read -- The method --
Column 4, line 48, reads "A method" should read -- The method --
Column 4, line 49, reads "soluble allergen" should read -- soluble wasp poison allergen --
Column 4, line 59, reads "A method" should read -- The method --

Signed and Sealed this

Twenty-ninth Day of April, 2008

JON W. DUDAS
*Director of the United States Patent and Trademark Office*